(12) United States Patent
Snow

(10) Patent No.: US 8,740,931 B2
(45) Date of Patent: Jun. 3, 2014

(54) VASCULAR FILTER

(75) Inventor: Jeremy W. Snow, South Jordan, UT (US)

(73) Assignee: Merit Medical Systems, Inc., South Jordan, UT (US)

( * ) Notice: Subject to any disclaimer, the term of this patent is extended or adjusted under 35 U.S.C. 154(b) by 175 days.

(21) Appl. No.: 13/204,492

(22) Filed: Aug. 5, 2011

(65) Prior Publication Data

US 2013/0035714 A1    Feb. 7, 2013

(51) Int. Cl.
*A61M 29/00*    (2006.01)

(52) U.S. Cl.
USPC ........................................................ 606/200

(58) Field of Classification Search
USPC ........................................ 606/198, 159, 200
See application file for complete search history.

(56) References Cited

U.S. PATENT DOCUMENTS

| | | |
|---|---|---|
| 4,132,650 A | 1/1979 | Krisch et al. |
| 4,494,531 A | 1/1985 | Gianturco |
| 4,619,246 A | 10/1986 | Molgaard-Nielsen |
| 4,781,177 A | 11/1988 | Lebigot |
| 4,832,055 A | 5/1989 | Palestrant |
| 4,900,312 A | 2/1990 | Nadeau |
| 5,133,733 A | 7/1992 | Rasmussen et al. |
| 5,234,458 A | 8/1993 | Metais |
| 5,242,462 A | 9/1993 | El-Nounou et al. |
| 5,312,479 A | 5/1994 | Weinstein et al. |
| 5,324,304 A | 6/1994 | Rasmussen |
| 5,370,657 A | 12/1994 | Irie |
| 5,375,612 A | 12/1994 | Cottenceau et al. |
| 5,437,655 A | 8/1995 | Bartholomew |
| 5,484,474 A | 1/1996 | Weinstein et al. |
| 5,601,568 A | 2/1997 | Chevillon et al. |
| 5,626,605 A | 5/1997 | Irie |
| 5,634,942 A | 6/1997 | Chevillon et al. |
| 5,669,933 A | 9/1997 | Simon |
| 5,709,704 A | 1/1998 | Nott et al. |
| 5,795,322 A | 8/1998 | Boudewijn |
| 5,810,874 A | 9/1998 | Lefebvre |
| 5,836,968 A | 11/1998 | Simon et al. |
| 5,836,969 A | 11/1998 | Kim |
| 5,853,420 A | 12/1998 | Chevillon et al. |
| 5,879,381 A | 3/1999 | Moriuchi |
| 5,954,741 A | 9/1999 | Fox |
| 5,976,172 A | 11/1999 | Homsma et al. |
| 5,984,947 A | 11/1999 | Smith |
| 6,007,558 A | 12/1999 | Ravenscroft et al. |
| 6,013,093 A | 1/2000 | Nott et al. |

(Continued)

FOREIGN PATENT DOCUMENTS

WO    WO2010091118    8/2010

OTHER PUBLICATIONS

Office Action dated Sep. 26, 2012 for U.S. Appl. No. 12/722,484.
Restriction Requirement dated Nov. 21, 2011 for U.S. Appl. No. 12/722,484.
Office Action dated Mar. 6, 2012 for U.S. Appl. No. 12/722,484.
U.S. Appl. No. 13/774,598, filed Feb. 22, 2013, Snow.

(Continued)

*Primary Examiner* — Tuan V Nguyen
(74) *Attorney, Agent, or Firm* — Stoel Rives LLP

(57) ABSTRACT

A filter, configured to be disposed within a body lumen, that includes one or more filtering zones. The filter may include one or more sets of legs, configured to interact with the body lumen wall in order to stabilize the position of the filter and to create a filtering structure. In some embodiments the filter may be integrally formed form a single tube of material.

27 Claims, 6 Drawing Sheets

(56) References Cited

U.S. PATENT DOCUMENTS

| | | |
|---|---|---|
| 6,059,825 A | 5/2000 | Hobbs |
| 6,099,549 A | 8/2000 | Bosma et al. |
| 6,117,165 A | 9/2000 | Becker |
| 6,156,055 A | 12/2000 | Ravenscroft |
| 6,193,739 B1 | 2/2001 | Chevillon et al. |
| 6,214,025 B1 | 4/2001 | Thistle et al. |
| 6,241,746 B1 | 6/2001 | Bosma et al. |
| 6,258,026 B1 | 7/2001 | Ravenscroft et al. |
| 6,267,777 B1 | 7/2001 | Bosma et al. |
| 6,273,900 B1 | 8/2001 | Nott et al. |
| 6,273,901 B1 * | 8/2001 | Whitcher et al. ............. 606/200 |
| 6,306,141 B1 | 10/2001 | Jervis |
| 6,328,719 B1 | 12/2001 | Holtermann et al. |
| 6,347,711 B1 | 2/2002 | Goebel et al. |
| 6,391,045 B1 | 5/2002 | Kim |
| 6,428,559 B1 | 8/2002 | Johnson |
| 6,436,121 B1 | 8/2002 | Blom |
| 6,443,972 B1 | 9/2002 | Bosma |
| 6,461,370 B1 | 10/2002 | Gray et al. |
| 6,468,290 B1 | 10/2002 | Weldon et al. |
| 6,485,501 B1 | 11/2002 | Green |
| 6,506,205 B2 | 1/2003 | Goldberg et al. |
| 6,511,496 B1 | 1/2003 | Huter et al. |
| 6,527,962 B1 | 3/2003 | Nadal |
| 6,540,722 B1 | 4/2003 | Boyle et al. |
| 6,540,768 B1 | 4/2003 | Diaz et al. |
| 6,589,266 B2 | 7/2003 | Whitcher et al. |
| 6,596,011 B2 | 7/2003 | Johnson et al. |
| 6,620,183 B2 | 9/2003 | DiMatteo |
| 6,623,506 B2 | 9/2003 | McGuckin, Jr. et al. |
| 6,656,203 B2 | 12/2003 | Roth et al. |
| 6,660,021 B1 | 12/2003 | Palmer et al. |
| 6,726,701 B2 | 4/2004 | Gilson |
| 6,783,538 B2 | 8/2004 | McGuckin, Jr. et al. |
| 6,793,665 B2 | 9/2004 | McGuckin, Jr. et al. |
| 6,932,831 B2 | 8/2005 | Forber |
| 6,939,361 B1 | 9/2005 | Kleshinski |
| 6,958,074 B2 | 10/2005 | Russell |
| 6,989,021 B2 | 1/2006 | Bosma |
| 6,991,641 B2 | 1/2006 | Diaz et al. |
| 7,147,649 B2 | 12/2006 | Thomas |
| 7,179,275 B2 | 2/2007 | McGuckin |
| 7,261,731 B2 | 8/2007 | Patel |
| 7,279,000 B2 | 10/2007 | Cartier et al. |
| 7,314,477 B1 | 1/2008 | Ravenscroft et al. |
| 7,323,002 B2 | 1/2008 | Johnson et al. |
| 7,329,227 B2 | 2/2008 | Schramm |
| 7,329,269 B2 | 2/2008 | Shapiro et al. |
| 7,338,512 B2 | 3/2008 | McGuckin, Jr. et al. |
| 7,344,549 B2 | 3/2008 | Boyle et al. |
| 7,399,308 B2 | 7/2008 | Borillo et al. |
| 7,534,251 B2 | 5/2009 | WasDyke |
| 7,544,202 B2 | 6/2009 | Cartier et al. |
| 7,582,100 B2 | 9/2009 | Johnson |
| 7,625,390 B2 | 12/2009 | Hendriksen et al. |
| 7,699,865 B2 | 4/2010 | Johnson et al. |
| 7,699,867 B2 | 4/2010 | Hendriksen et al. |
| 7,704,266 B2 | 4/2010 | Thinnes, Jr. et al. |
| 7,704,267 B2 | 4/2010 | Tessmer |
| 7,736,383 B2 | 6/2010 | Bressler et al. |
| 7,749,246 B2 * | 7/2010 | McGuckin et al. ........... 606/200 |
| 7,763,045 B2 | 7/2010 | Osborne |
| 7,771,452 B2 | 8/2010 | Pal et al. |
| 7,780,694 B2 | 8/2010 | Palmer et al. |
| 7,794,473 B2 | 9/2010 | Tessmer et al. |
| 7,803,171 B1 | 9/2010 | Uflacker |
| 7,862,577 B2 | 1/2011 | Gray et al. |
| 7,887,561 B2 | 2/2011 | McGuckin, Jr. et al. |
| 7,909,847 B2 | 3/2011 | McGuckin, Jr. et al. |
| 7,931,664 B2 | 4/2011 | Gray et al. |
| 7,959,647 B2 | 6/2011 | Palmer |
| 7,967,838 B2 | 6/2011 | Chanduszko et al. |
| 7,972,353 B2 | 7/2011 | Hendriksen et al. |
| 7,976,562 B2 | 7/2011 | Bressler et al. |
| 7,996,993 B2 | 8/2011 | Gray et al. |
| 8,025,675 B2 | 9/2011 | Shirley et al. |
| 8,029,529 B1 | 10/2011 | Chankduszko |
| 8,043,322 B2 | 10/2011 | Hendriksen et al. |
| 8,057,506 B2 | 11/2011 | Gilson et al. |
| 8,057,507 B2 | 11/2011 | Horan et al. |
| 8,062,326 B2 | 11/2011 | McGuckin, Jr. et al. |
| 8,062,327 B2 | 11/2011 | Chanduszko et al. |
| 8,062,328 B2 * | 11/2011 | Hallisey ........................ 606/200 |
| 8,092,484 B2 | 1/2012 | Kashkarov et al. |
| 8,092,485 B2 | 1/2012 | Lapid |
| 8,100,936 B2 | 1/2012 | McGuckin, Jr. et al. |
| 8,105,349 B2 | 1/2012 | Hendriksen et al. |
| 8,118,828 B2 | 2/2012 | Cartier et al. |
| 8,133,251 B2 | 3/2012 | Ravenscroft et al. |
| 8,133,252 B2 | 3/2012 | Davis et al. |
| 8,162,972 B2 | 4/2012 | McGuckin, Jr. et al. |
| 8,167,901 B2 | 5/2012 | Hendriksen et al. |
| 8,211,140 B2 | 7/2012 | McGunkin, Jr. et al. |
| 8,246,648 B2 | 8/2012 | Tekulve |
| 8,246,650 B2 | 8/2012 | Osborne |
| 8,246,651 B2 | 8/2012 | Hendriksen et al. |
| 8,252,017 B2 | 8/2012 | Paul, Jr. et al. |
| 8,252,019 B2 | 8/2012 | Fleming, III |
| 8,267,954 B2 | 9/2012 | Decant, Jr. et al. |
| 8,282,668 B2 | 10/2012 | McGuckin, Jr. et al. |
| 8,317,818 B2 | 11/2012 | Kashkarov et al. |
| 8,333,785 B2 | 12/2012 | Chanduszko et al. |
| 8,353,926 B2 | 1/2013 | Silver |
| 8,366,736 B2 | 2/2013 | Thinnes, Jr. et al. |
| 8,383,926 B2 | 2/2013 | Plissonnier et al. |
| 2001/0000799 A1 | 5/2001 | Wessman et al. |
| 2001/0039432 A1 | 11/2001 | Whitcher et al. |
| 2002/0058911 A1 | 5/2002 | Gilson et al. |
| 2002/0062134 A1 | 5/2002 | Barbut et al. |
| 2002/0111647 A1 | 8/2002 | Khairkhahan et al. |
| 2003/0109897 A1 | 6/2003 | Walak et al. |
| 2004/0116959 A1 | 6/2004 | McGuckin |
| 2004/0220610 A1 | 11/2004 | Kriedler et al. |
| 2005/0004596 A1 | 1/2005 | McGuckin, Jr. et al. |
| 2005/0015111 A1 | 1/2005 | McGuckin et al. |
| 2005/0080447 A1 | 4/2005 | McCuckin, Jr. et al. |
| 2005/0222604 A1 | 10/2005 | Shaeffer |
| 2005/0267515 A1 | 12/2005 | Oliva et al. |
| 2005/0288704 A1 | 12/2005 | Cartier et al. |
| 2005/0288705 A1 | 12/2005 | Gilson |
| 2006/0009799 A1 | 1/2006 | Kleshinski et al. |
| 2006/0041271 A1 | 2/2006 | Bosma et al. |
| 2006/0079928 A1 | 4/2006 | Cartier |
| 2006/0079930 A1 | 4/2006 | McGuckin et al. |
| 2006/0100659 A1 | 5/2006 | Dinh et al. |
| 2006/0106417 A1 | 5/2006 | Tessmer |
| 2006/0206138 A1 | 9/2006 | Eidenschink |
| 2007/0005095 A1 | 1/2007 | Osborne |
| 2007/0141107 A1 | 6/2007 | Kutryk |
| 2007/0162048 A1 | 7/2007 | Quinn et al. |
| 2007/0167974 A1 | 7/2007 | Cully et al. |
| 2007/0173885 A1 | 7/2007 | Cartier |
| 2007/0191932 A1 | 8/2007 | Kutryk |
| 2007/0198050 A1 | 8/2007 | Ravenscroft |
| 2008/0027481 A1 | 1/2008 | Gilson |
| 2008/0033479 A1 | 2/2008 | Silver |
| 2008/0097518 A1 | 4/2008 | Thinnes |
| 2008/0234722 A1 | 9/2008 | Bonnette et al. |
| 2008/0275487 A1 | 11/2008 | Fleming |
| 2008/0275492 A1 | 11/2008 | Farmiga |
| 2009/0043332 A1 | 2/2009 | Sullivan et al. |
| 2009/0069840 A1 | 3/2009 | Hallisey |
| 2009/0198270 A1 | 8/2009 | McGuckin, Jr. et al. |
| 2009/0254117 A1 | 10/2009 | Pakter |
| 2009/0299403 A1 | 12/2009 | Chanduszko et al. |
| 2009/0299404 A1 | 12/2009 | Chanduszko et al. |
| 2010/0049238 A1 | 2/2010 | Simpson |
| 2010/0174310 A1 | 7/2010 | Tessmer |
| 2010/0185229 A1 | 7/2010 | Horan et al. |
| 2010/0185230 A1 | 7/2010 | Horan et al. |
| 2010/0198252 A1 | 8/2010 | Beyer et al. |
| 2010/0318115 A1 | 12/2010 | Chanduszko et al. |
| 2011/0040321 A1 | 2/2011 | Cartier |
| 2011/0106133 A1 | 5/2011 | O'Connell et al. |

(56) References Cited

U.S. PATENT DOCUMENTS

| | | | |
|---|---|---|---|
| 2011/0137335 A1* | 6/2011 | Hallisey | 606/200 |
| 2011/0166593 A1 | 7/2011 | Paul, Jr. | |
| 2011/0202086 A1 | 8/2011 | Bates | |
| 2011/0208233 A1 | 8/2011 | McGuckin, Jr. et al. | |
| 2012/0089173 A1 | 4/2012 | Tukulve | |
| 2012/0109181 A1 | 5/2012 | Hallisey | |
| 2012/0130418 A1 | 5/2012 | Jenson et al. | |
| 2012/0184985 A1 | 7/2012 | Ravenscroft et al. | |
| 2012/0245622 A1 | 9/2012 | McGuckin, Jr. et al. | |
| 2013/0018387 A1 | 1/2013 | Diamant | |
| 2013/0035713 A1 | 2/2013 | Snow | |

OTHER PUBLICATIONS

International Search and Written Opinion dated Jun. 13, 2013 for PCT/US2013/027427.
U.S. Appl. No. 13/204,462, filed Aug. 5, 2011, Snow.
Boothroyd et al., 'Product Design for Manufacture and Assembly.' 1994, p. 64.
International Preliminary Report for Application No. PCT/US08/75102 dated Mar. 9, 2010.
International Publication and Written Opinion for Application No. PCT/US08/75102 dated Mar. 12, 2009.
Cipolla et al., 'Complications of Vena Cava Filters: A Comprehensive Clinical Review.' OPUS 12 Scientist 2008; vol. 2, No. 2: 11-24.
Katsamouris et al. 'Inferior Vena Cava Filters: In Vitro Comparison of Clot Trapping and Flow Dynamics.' Radiology 1988; 166:361-366.
Prince et al., 'The diameter of the inferior Vena Cava and It's Implications for the Use of Vena Caval Filters.' Radiology 1983; 149:687-689.
Simon et al., 'Comparative Evaluation of Clinically Available Inferior Vena Cava Filters with an In Vitro Physiologic Simulation of the Vena Cava.' Radiology 1993; 189:769-774.
Lorch et al., 'In Vitro Studies of Temporary Vena Cava Filters.' CardioVascular and Interventional Radiology 1998; 21:146-150.
Neuerburg et al., 'New Retrievable Percutaneous Vena Cava Filter: Experimental In Vitro and In Vivo Evaluation.' CardioVascular and Interventional Radiology 1993: 16:224-229.
Reekers et al., 'Evaluation of the Retrievability of the OptEase IVC Filter in an Animal Model.' J Vasc Interv Radiol 2004; 15:261-267.
Kinney, 'Update on Inferior Vena Cava Filters.' J Vasc Interv Radiol 2003; 14:425-440.
Bruckheimer et al., 'In Vitro Evaluation of a Retrievable Low-Profile Nitinol Vena Cava Filter.' J Vasc Interv Radiol 2003; 14:469-474.
Brountzos et al., 'A New Optional Vena Cava Filter: Retrieval at 12 Weeks in an Animal Model.' J Vasc Interv Radiol 2003; 14:763-772.
Ray et al., 'Outcomes with Retrievable Inferior Vena Cava Filters: A Multicenter Study.' J Vasc Interv Radiol 2006; 17:1595-1604.
Kaufman et al., 'Guidelines for the Use of Retrievable and Convertible Vena Cava Filters: Report from the Society of Interventional Radiology Mulitdisciplinary consensus conference.' J Vasc Interv Radiol 2006; 17:449-459.
Kolbeck et al., 'Optional Inferior Vena Cava Filter Retrieval with Retained Thrombus: An In Vitro Model.' J Vasc Interv Radiol 2006; 17:685-691.
Lorch et al., 'Current Practice of Temporary Vena Cava Filter Insertion: A Multicenter Registry.' JVIR 2000; 11:83-88.
Rousseau et al., 'The 6-F Nitinol TrapEase Inferior Vena Cava Filter: Results of a Prospective Multicenter Trial.' J Vasc Interv Radiol 2001; 12:299-304.
Stoneham et al., 'Temporary Inferior Vena Cava Filters: In Vitro Comparison with Permanent IVC Filters.' JVIR 1995; 6:731-736.
Crochet et al., 'Evaluation of the LGM Vena Cava-Tech Infrarenal Vena Cava Filter in and Ovine Venous Thromboembolism Model.' J Vasc Interv Radiol 2001; 12:739-745.
Kaufman, 'Guidelines for the Use of Optional Retrievable Vena Cava Filters.' European Respiratory Disease 2007; 31-34.
Epstein et al., 'Experience with the Amplatz Retrievable Vena Cava Filter.' Radiology 1989; 172:105-110.

Inferior Vena Cava Filter, ISI Interventional & Surgical Innovations LLC. Product Brochure, Copyright 2008.
The Clot Stopper (online). Retrieved from the internet URL:http://www.americanheritage.com/people/articles/web/20060715-pulmonary-embolism-blood-clot-lazar-greenfield-garman-kimmel-surgery-medical-doctor-surgeon.shtml Summer 2006, vol. 22 Issue 1.
Simon Nitinol Filter, Versatile and Dependable Performance. Bard Peripheral Vascular (online). Retrieved from the internet URL:http://www.bardpv.com_vascular/product.php?p=23 Copyright 2004.
Aegisy Vena Cava Filter. Shenzhen Lifetech Scientific Inc. (online). Retrieved from the internet URL:http://www.lifetechmed.com/english/product/product6.htm Copyright 2005.
Safe Flo Vena Cava Filter (online). Retrieved from the internet <URL:www.rafaelmedical.com>.
Aegisy Vena Cava Filter Product Description (online). Retrieved from the internet URL:http://www.lifetechclinic.com/upload/article/vena/instruction_for_use.htm Accessed Jun. 6, 2008.
Design History (online). Retrieved from the internet URL:http://www.lifetechclinic.com/upload/article/vena/vena_cava_filter.htm Jun. 6, 2008.
Crux Biomedical, Inc. Inferior Vena Cava Filter System Instructions for Use, IFU P/N 0001 Rev.B, DCO# 0027, Effective Date Feb. 2, 2007.
Smouse, 'Next Generation Filters: Are There Improvements Over the Existing Filters?', Powerpoint Presentation. University of Illinois College of Medicine at Peoria.
Kaufman, 'Vena Cava Filters as a Risk Factor for VTE'. Powerpoint Presentation at the SIR Foundation Jun. 2007 IVC Filter Research Consensus Panel.
Rectenwald, 'Are All IVC's the Same.' Powerpoint Presentation at the SIR Foundation Jun. 2007 IVC Filter Research Consensus Panel.
Rogers, 'Vena Cava Filter Outcomes.' Powerpoint Presentation at the SIR Foundation Jun. 2007 IVC Filter Research Consensus Panel.
SIR Foundation Research Consensus Panel for the Development of a Research Agenda in Inferior Vena Cava Filters, Jun. 12, 2007—Herndon, VA. Powerpoint Presentation at the SIR Foundation Jun. 2007 IVC Filter Research Consensus Panel.
TrapEase Vena Cava Filter User's Instruction. Cordis Corp.
Corriere et al., 'Vena Cava Filters: An Update.' Future Cardiol 2006: 2(6): 695-707.
Mohan, C. et al. 'Comparative Efficacy and Complications of Vena Caval Filters.' J Vasc Surg 1995; 21:235-246.
Linsenmaier, U. et al., 'Indications, Management, and Complications of Temporary Inferior Vena Cava Filters.' Cardiovascular Intervent, Radiol 1998; 21(6): 464-469.
Asch et al. Radiology 2002; 29:173-176.
Cunliffe et al., 'A Fatal Complication of a Vena Cava Filter Associated with Pulmonary Thromboembolism.' Am J Forensic Med Pathol 2008; 29:173-176.
Joels et al., 'Complications of Inferior Vena Cava Filters.' Am Surg 2003; 69:654-659.
Pulmonary Embolism (online). Retrieved from internet URL:http://www.mayoclinic.com/health/pulmonary-embolism/DS00429/DSECTION=complications By Mayo Clinic Staff Sep. 28, 2007.
Cordis TrapEase Permanent Vena Cava Filter with the VisEase Angiographic Vessel Dilator (on line). Retrieved from <URL:http//www.mitek.com/home.jhtml?loc=USENG&page=viewcontent&contentid=09008b9880ffdcbf&nodekey=1Prod_Info/Type/Endovascular_Disease_Management/Vena_Cava_Filters&parentid=fc0de00100001215> 2000-2008.
Decousus et al., 'A Clinical Trial of Vena Caval Filters in the Prevention of Pulmonary Embolism in Patients with Proximal Deep-Vein Thrombosis.' The New England Journal of Medicine, Feb. 12, 1998; vol. 338, No. 7.
Notice of Allowance for U.S. Appl. No. 12/203,515 dated Jul. 13, 2011.
International Search Report and Written Opinion dated Jan. 30, 2013 for PCT/US2012/047004.
International Search Report and Written Opinion dated Jan. 30, 2013 for PCT/US2012/047023.

* cited by examiner

VASCULAR FILTER

TECHNICAL FIELD

The present disclosure relates generally to filters configured to be disposed within a body lumen. More particularly, the present disclosure relates to filters or similar devices that may be configured to capture blood clots within the vasculature, such as within the inferior vena cava.

BRIEF DESCRIPTION OF THE DRAWINGS

The embodiments disclosed herein will become more fully apparent from the following description and appended claims, taken in conjunction with the accompanying drawings. These drawings depict only typical embodiments, which will be described with additional specificity and detail through use of the accompanying drawings in which:

FIG. 1A is a detail view, taken through line 1A-1A, of a portion of the filter of FIG. 1.

FIG. 1B is a detail view, taken through line 1B-1B, of a portion of the filter of FIG. 1.

DETAILED DESCRIPTION

A filter may be configured to be disposed within the vasculature to capture or trap material within a body lumen. For example, a filter may be configured to trap blood clots in the vasculature. In some embodiments, a filter may be disposed within the inferior vena cava and be configured to inhibit pulmonary embolism. Furthermore, a filter may be configured to be removable.

Though many of the examples provided herein may refer to a filter disposed within the inferior vena cava, the present disclosure is applicable to a variety of filters configured to be disposed elsewhere within the vasculature or within other body lumens.

It will be readily understood that the components of the embodiments, as generally described and illustrated in the figures herein, could be arranged and designed in a variety of configurations. Thus, the following more detailed description of various embodiments, as represented in the figures, is not intended to limit the scope of the disclosure, but is merely representative of various embodiments. While the various aspects of the embodiments are presented in drawings, the drawings are not necessarily drawn to scale unless specifically indicated.

The phrases "connected to," "coupled to," and "in communication with" refer to any form of interaction between two or more entities, including mechanical, electrical, magnetic, electromagnetic, fluid, and thermal interaction. Two components may be coupled to each other even though they are not in direct contact with each other. For example, two components may be coupled to each other through an intermediate component.

The terms "proximal" and "distal" refer to opposite ends of a medical device. As used herein, the proximal end of a medical device is the end nearest a practitioner while the practitioner is placing or manipulating the device, while the distal end is the opposite end. For example, the proximal end of a filter refers to the end nearest the practitioner when the filter is disposed within, or being deployed from, a deployment device. For consistency throughout, these terms remain constant in the case of a deployed filter, regardless of the orientation of the filter within the body.

Figure 1:
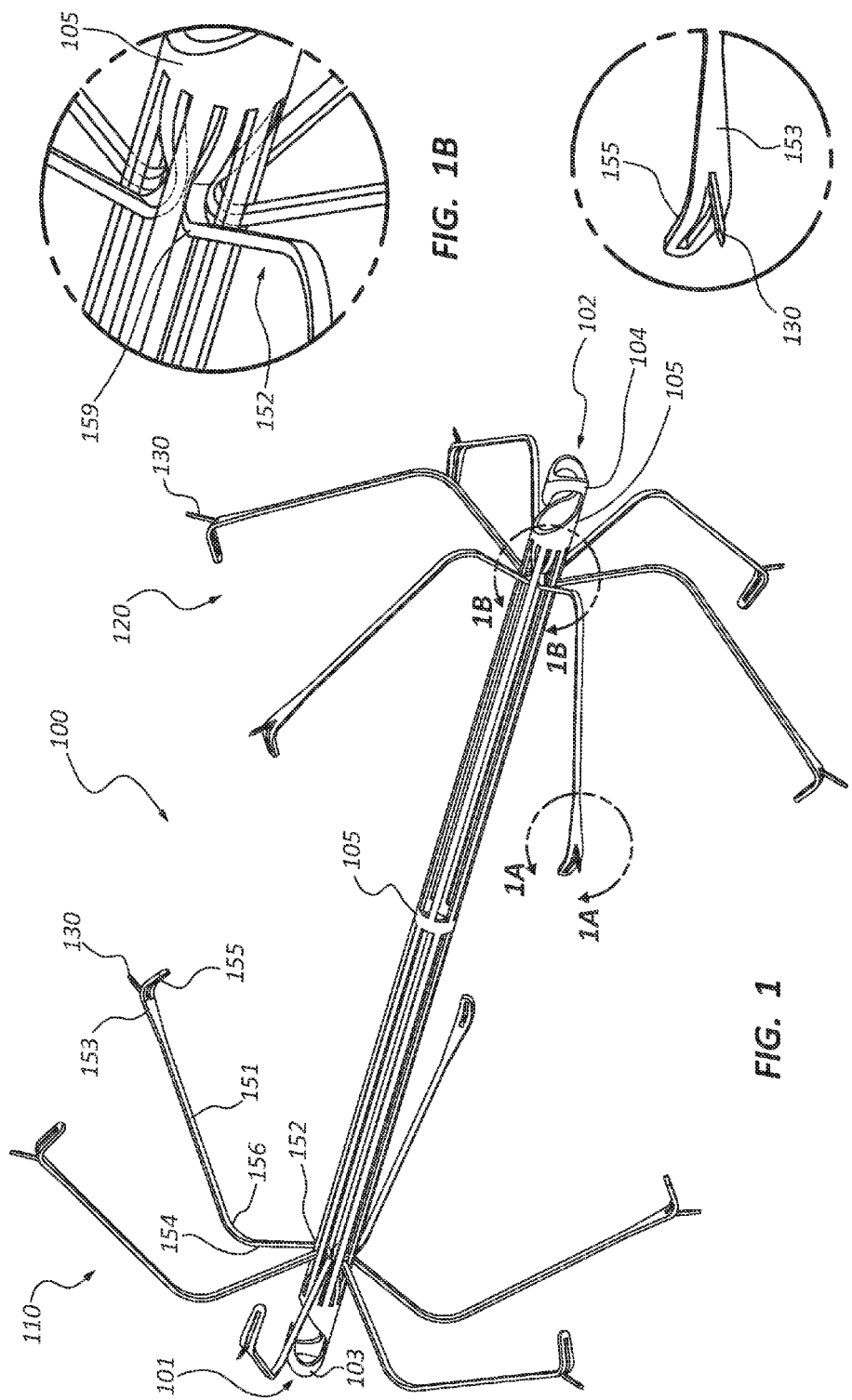
FIG. 1 is a perspective view of a filter.

FIG. 1 is a perspective of a filter 100. The filter 100 of FIG. 1 has a proximal hook 103 coupled to the proximal end 101 of the filter 100 and a distal hook 104 coupled to the distal end 102 of the filter 100. Further, the filter 100 has an axial member, tubular portion 105, which runs from the proximal end 101 of the filter 100 to the distal end 102. The tubular portion 105 runs the entire length of the filter 100, though the tubular structure is "perforated" due to the removal of material along the tube for the legs 110, 120 and other components. In other embodiments, the axial member may or may not be formed in a tubular shape.

As used herein, the center axis of the filter refers to the radial centerline of the filter in the axial direction. In embodiments with a tubular axial member, the center axis of the filter is the center axis of the tubular axial member.

In some embodiments, the filter 100 includes a first set of legs 110 and a second set of legs 120. The legs of the first set of legs 110 may be circumferentially positioned around the tubular portion 105. In some embodiments, such as the illustrated embodiment, each leg of the first set of legs 110 may be coupled to the tubular portion 105 at the same axial location along the length of the tubular portion 105. In the illustrated embodiment, the first set of legs 110 comprises six legs; in other embodiments the first set of legs 110 may comprise more or fewer legs, including embodiments with three, four, five, seven, eight, nine, and ten legs comprising the first set of legs 110.

The two sets of legs 110, 120 in the illustrated embodiment are mirror images of each other, mirrored about the longitudinal midpoint of the filter 100 and offset in the circumferential direction. Thus, any disclosure provided in connection with one set of legs may be applicable to the other set. For example, disclosure recited above concerning the number, arrangement, and shape of the first set of legs 110 is analogously applicable to the second set of legs 120 as well. Notwithstanding this "mirror image" relationship, the two sets of legs 110, 120 may be longitudinally or circumferentially offset from each other more or less than shown in the illustrated embodiment.

Each leg may include an inner end 152 coupled to the tubular portion 105, a first portion 151, and a free end 153. The leg may be configured to extend radially outward from the center axis of the filter 100, from the inner end 152 to the free end 153. An outer portion 155 of the free end 153 may be configured to curve back toward the center axis of the filter 100. Further, a barb 130 may also be coupled to the free end 153 of the leg.

In other embodiments, individual legs of each set may be shaped or oriented differently than shown in FIG. 1, including embodiments where legs within a set of legs have different shapes and/or embodiments where the two sets of legs have different shapes and/or orientations.

In the illustrated embodiment, outer portion 155 may be curved or otherwise configured to prevent the free end 153 from extending into, or piercing, a body lumen wall. The curvature of the outer portion 155 may create a smooth, rounded contact surface between the filter leg and the body lumen wall. The barb 130 may be configured to prevent the rounded free end 153 from migrating with respect to a body lumen wall. In some embodiments, the outer portion 155 may act as a "stop," restricting the length to which the barb 130 may extend into the lumen wall. The relative positions of these components in the illustrated embodiment are shown in detail in FIG. 1A.

As also shown in FIG. 1A the barbs 130 may be cut from a central portion of the filter legs in some embodiments, by a substantially U-shaped cut. In other embodiments the barbs 130 may be formed from other parts of the legs, or formed from a different piece of material and coupled to the legs. While in the embodiment of FIG. 1, each leg of the first set of legs 110 and each leg of the second set of legs 120 is coupled to a barb 130, in other embodiments barbs may only be located on either the first set of legs 110, only the second set of legs 120, or only certain individual legs of the first 110 and/or second 120 sets of legs.

In the illustrated embodiment, the barbs 130 are oriented such that the barbs 130 associated with the first set of legs 110 face the opposite direction from the barbs 130 associated with the second set of legs 120. Specifically, in the illustrated embodiment, the barbs 130 associated with the first set of legs 110 are oriented such that each barb 130 extends from the leg toward to the distal end 102 of the filter 100, and the barbs 130 associated with the second set of legs 120 extend toward the proximal 101 end of the filter 100. In some embodiments, bi-directional barbs, or barbs 130 thus oriented in opposite directions, may be configured to prevent migration of the filter 100 in either direction along a body lumen. In other words, each barb 130 may be configured to generally prevent migration of the filter 100 in the direction the barb 130 is oriented; thus, filters with bi-directional barbs 130 may be configured to resist migration in both directions.

Further, as shown in FIG. 1 and in the detail view of FIG. 1B, in some embodiments a filter may be configured such that the inner ends 152 of the legs couple to the tubular portion 105 through an intermediate curved portion 159. The curved portion 159 may be configured to distribute stress in the leg, particularly when the leg is drawn within a catheter (discussed further in connection with FIG. 4). The curved portion 159 may thus minimize the potential for kinking or other plastic deformation by so distributing the load and stress at the coupling point between the legs 110, 120 and the tubular portion 105.

Additionally, in certain embodiments, including those illustrated, each leg may include a second substantially straight portion 154 coupled to the inner end 152, either directly or via, for example, curved portion 159, and also coupled to the first portion 151, which is also substantially straight, such that the second substantially straight portion 154 and first portion 151 define an angle of between about 90 degrees and about 180 degrees. In the embodiments shown in FIGS. 1-5, the second substantially straight portion 154 and the first portion 151 are connected by a curved shoulder 156. The outer surface of the substantially straight portion 154 and the outer surface of the tubular portion 105 define an acute angle.

Figure 2:
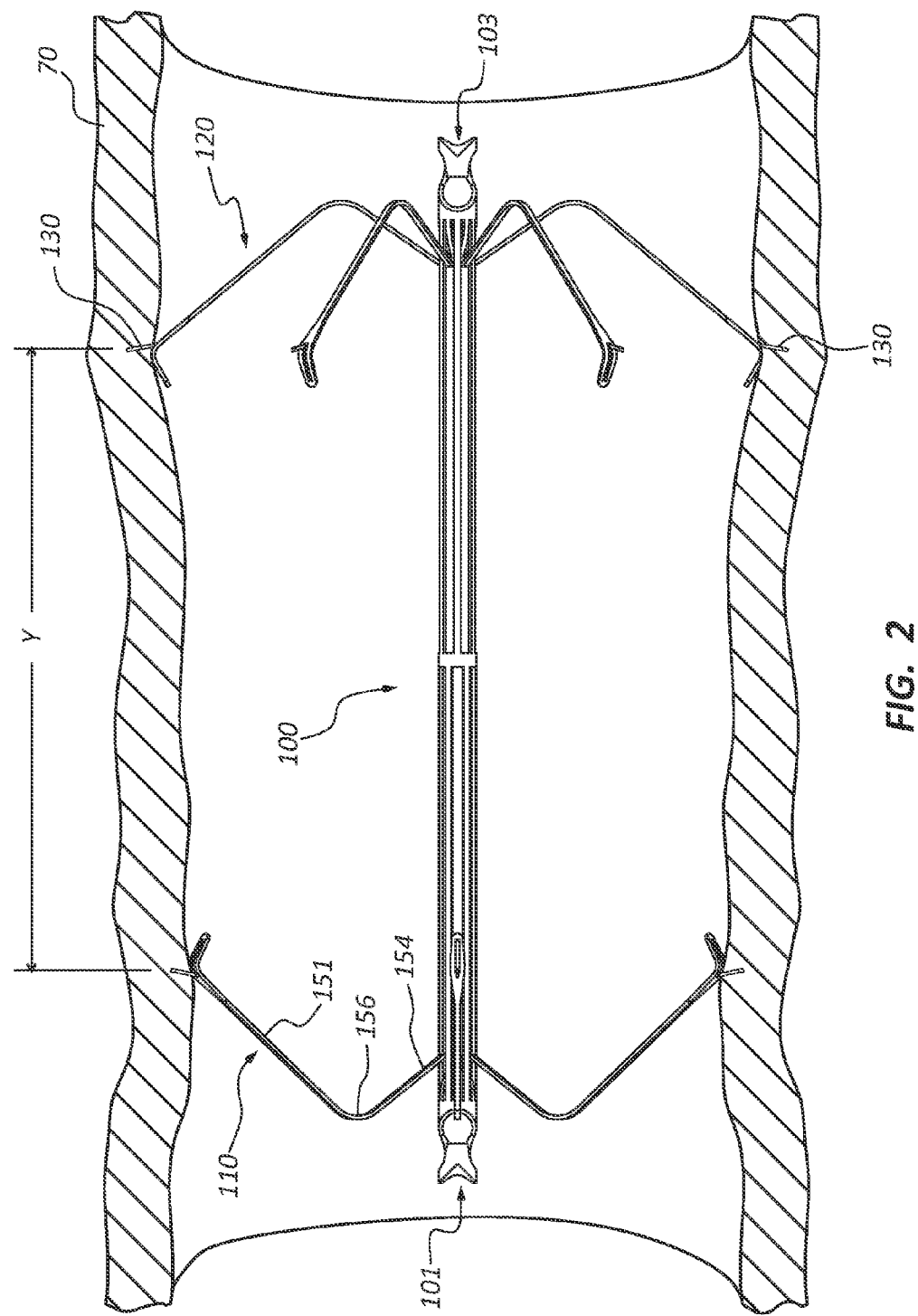
FIG. 2 is a side view of the filter of FIG. 1, disposed within a body lumen.

FIG. 2 is a side view of filter 100 disposed within a body lumen 70. In the drawing of FIG. 2, the body lumen 70 is shown as a cross section, while the filter 100 is not. The filter 100 is disposed within the body lumen 70 such that the filter 100 is substantially coaxially aligned with the body lumen 70. As shown in FIG. 2, distance Y, the longitudinal displacement of the first set of legs 110 with respect to the second set of legs 120, may affect the stability of the filter 100 in some instances. This distance, Y, may be from about 0.200 inches to about 1.000 inches. Contact between both the first set of legs 110 and the second set of legs 120 of the filter 100 and the lumen 70 may tend to keep the filter 100 centered within the body lumen 70. The displacement, Y, of the two sets of legs 110, 120 may minimize the degree to which the filter 100 can pivot on the contact between either set of legs 110, 120 and the lumen 70. Thus, the migration of either the proximal 101 or distal 103 end of the filter 100 toward the body lumen 70 wall may be prevented or minimized. Accordingly, in the event that a medical practitioner wishes to remove or relocate the filter 100, the hooks 103, 104 will remain spaced from the inner wall of the body lumen 70 and are readily accessible to the practitioner. Furthermore, in some applications the tendency of the filter 100 to remain centered within the lumen 70 may maintain the relative positions and orientations of the filtering zones within the lumen 70. FIG. 2 also shows the implantation of the barbs 130 in the body lumen 70 wall.

FIG. 2 further shows how the curved shoulder 156 connection between the second substantially straight portion 154 and first portion 151 may compress the filter zones in the longitudinal direction, i.e., potentially allowing the filter zone to occupy longitudinally less space within the body lumen 70. In some embodiments, legs configured with relatively small angles between the first portions 151 and the second substantially straight portions 154 may result in filter zones which occupy less longitudinal space than filter zones comprised of legs with larger angles.

Figure 3:
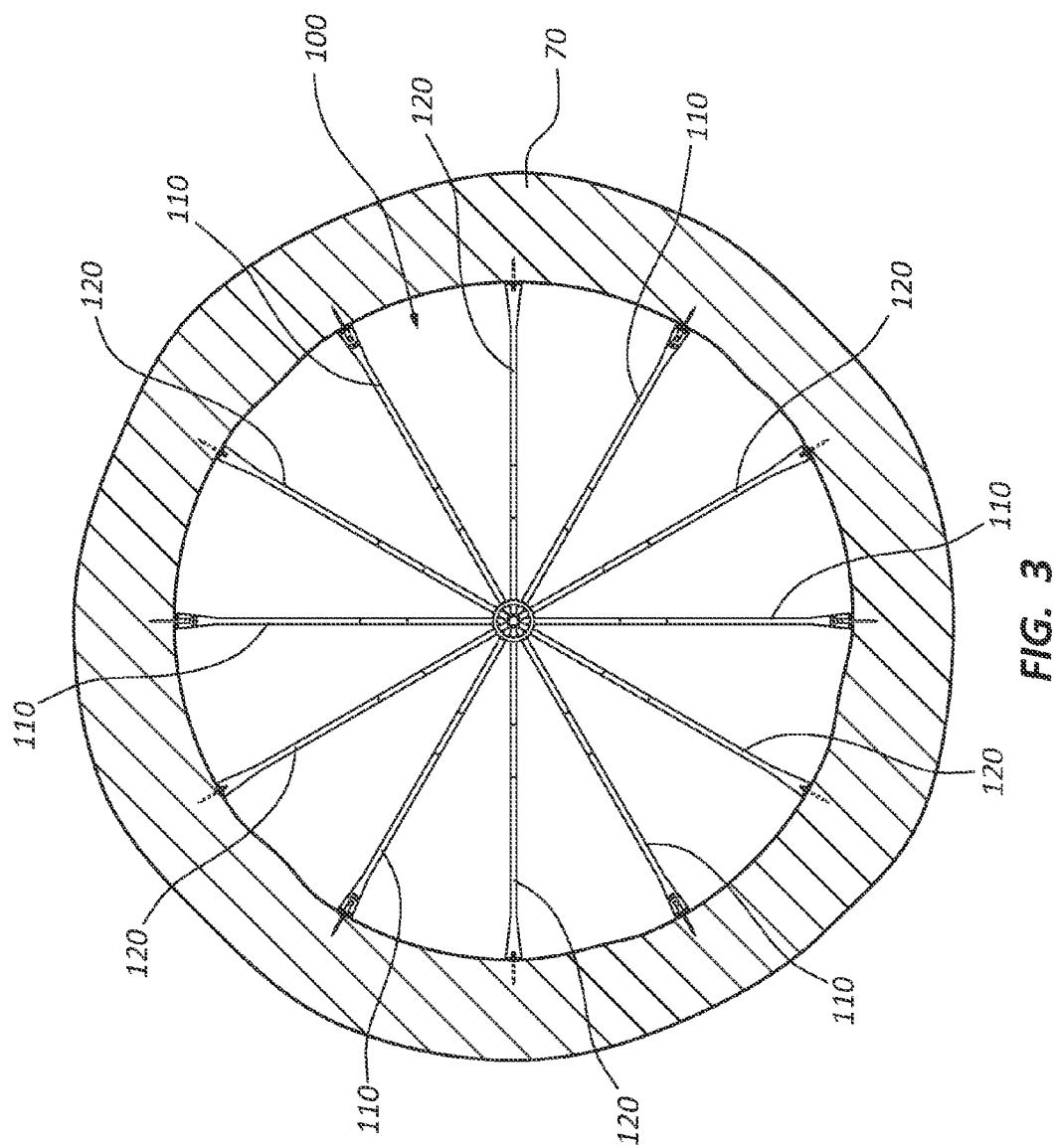
FIG. 3 is an end view of the filter of FIGS. 1 and 2, disposed within the body lumen of FIG. 2.

FIG. 3 is an end view of filter 100 disposed within a body lumen 70. As with FIG. 2, the filter 100 is not shown in cross section (it is shown in end projection), while the body lumen 70 is so shown. In the embodiment of FIG. 3, each of the legs 110 of the first set of legs is evenly spaced around the center axis of the filter 100. Likewise, each of the legs 120 of the second set of legs is also evenly spaced around the center axis of the filter 100. Furthermore, in the embodiment of FIG. 3, the legs of the second set of legs 120 are offset from the legs of the first set of legs 110, such that each leg of the second set of legs 120 is equally spaced between adjacent legs of the first set of legs 110 around the axis of the filter. In other embodiments, the first set of legs 110, the second set of legs 120, or both may not be evenly spaced or evenly offset.

Figure 4:
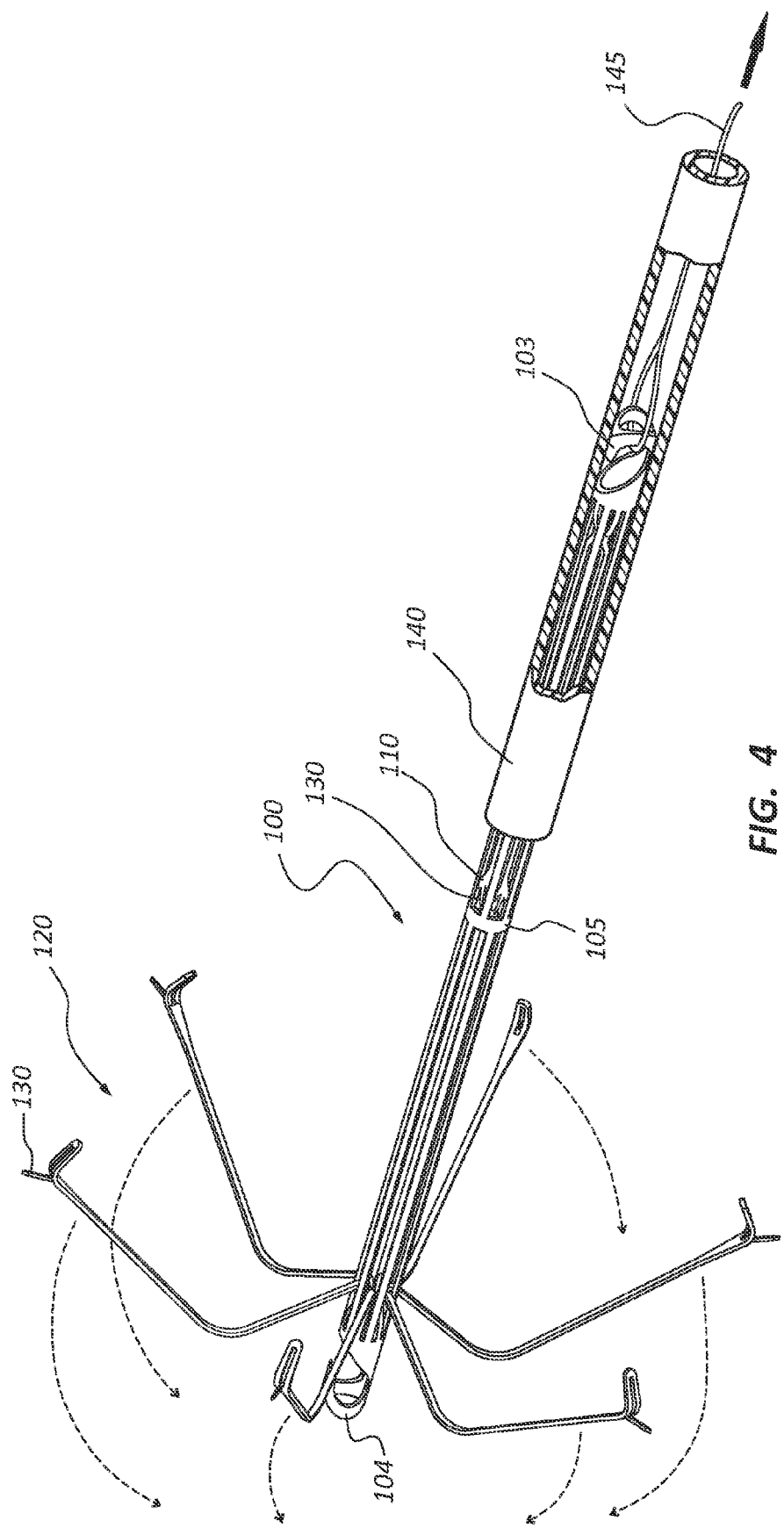
FIG. 4 is a perspective view of the filter of FIG. 1, partially disposed within a catheter.

FIG. 4 is a perspective view of filter 100, partially disposed within a catheter 140. In some instances, the legs 110, 120 may be contracted and the filter 100 disposed within a catheter 140 or other delivery device or sheath. In some embodiments, this may be accomplished by coupling a snare 145 disposed within a catheter 140 to one of the hooks 103, 104 of the filter 100. The filter 100 may then be drawn into the catheter 140 by displacing the snare 145 with respect to the catheter 140. This displacement may bring the first set of legs 110 and the second set of legs 120 into contact with the catheter 140, thereby causing the legs to fold down as the filter 100 is drawn into the catheter 140. In the illustration of FIG. 4, the arrows near the second set of legs 120 indicate the direction of displacement of the second set of legs 120 of the filter 100 as the filter 100 is drawn into the catheter 140.

As shown in FIG. 4, in some embodiments the set of legs first contacted by the catheter 140 (the first set of legs 110 in FIG. 4) may be configured to fold such that the free ends of the legs are disposed near the longitudinal midpoint of the filter 100 while the second set of legs contacted by the catheter 140 (the second set of legs 120 in FIG. 4) fold up beyond the hook at the distal end of the filter 100. In other words, both sets of legs 110, 120 may fold up distally or both sets of legs 110, 120 may fold up proximally, depending on which end of the filter 100 is drawn into the catheter 140.

In some embodiments, the filter 100 may be comprised of a shape memory alloy, for example nitinol. Thus, the filter 100 may be comprised of a material which, is first "set" in a particular shape when the filter 100 is being manufactured, then tends to return to that shape if it is subsequently deformed. The filter 100 may be "set" in the expanded configuration, or the shape generally shown in FIGS. 1-3. Drawing the filter 100 into a catheter 140, as shown in FIG. 4, may thus temporarily compress the legs 110, 120 within the catheter 140, though the filter 100 may be configured to return to the expanded shape upon deployment from the catheter 140.

In some embodiments, the legs 110, 120 of the filter 100 may form a general "umbrella shape." For example, in FIG. 4 the second set of legs 120 may be described as forming a general umbrella shape as they expand radially outward from the tubular member 105, while also generally curving such that the free ends of the legs are displaced from the base of the legs a distance along the center axis of the filter 100. Furthermore, the manner in which the legs 110, 120 are compressed within a catheter 140 may be generally analogous to the displacement of umbrella supports along the center handle of an umbrella when the umbrella is folded up. For example, in FIG. 4 the first set of legs 110 are compressed inwardly toward the tubular member 105 to a placement that may be analogous to the supports of a folded umbrella. Conversely, the second set of legs 120 of FIG. 4, are configured to first fold away from the tubular portion 105, in a "reverse umbrella" type manner. Thus, the legs 110, 120 of the filter 100 may be configured to be both compressible, as within a catheter 140, and expandable, as when the legs 110, 120 are deployed from a compressed configuration.

Referring to also FIG. 1B, which illustrates the intermediate portion 159 at the base of each leg in the illustrated embodiment, the intermediate portion 159 may be configured to allow the filter 100 to be drawn into a catheter without plastically deforming. More specifically, in the illustrated embodiment, the curved intermediate portion 159 is configured such that the intermediate portion 159 curves inward from the tubular portion 105 toward the axis of the filter, then curves outward toward the radially expanding legs. Thus, in some embodiments the intermediate portion 159 may form a compound curve which includes an inflection point. This curvature may be configured to distribute the stress associated with bending the legs 110, 120 into a catheter 140. In some embodiments, segments of one or both of the curves of the intermediate portion 159 may have radii from about 0.005 inches to about 0.150 inches.

The intermediate portion 159 may be configured to distribute stress in such a manner as to allow the legs 110, 120 to bend in toward the axis of the filter 100 directly, as the legs of the first set of legs 110 in FIG. 4, or to bend the opposite direction, away from the axis of the filter 110 as the legs of the second set of legs 120 in FIG. 4. In embodiments such as that of FIG. 4, the second set of legs to enter the catheter may undergo greater displacement (and greater stress) than the first set of legs to enter the catheter. The intermediate portion 159 may be configured to provide elasticity and resiliency to enable such bending.

The filter 100 may be drawn into the catheter 140 in order to use the catheter 140 to place the filter 100 within a body lumen of a patient. Furthermore, the filter 100 may be partially or fully drawn back into the catheter 140 after the filter 100 is placed within the body lumen, in order to move the filter 100 within the body lumen, or to completely remove the filter 100 from the body lumen. The filter 100 may therefore be configured to be removably or permanently disposed within a body lumen of a patient.

In some embodiments the filter 100 may be configured such that, when the filter 100 is deployed from a catheter 140, one set of legs 110, 120 engages the lumen walls before the other set of legs 110, 120.

Figure 5:
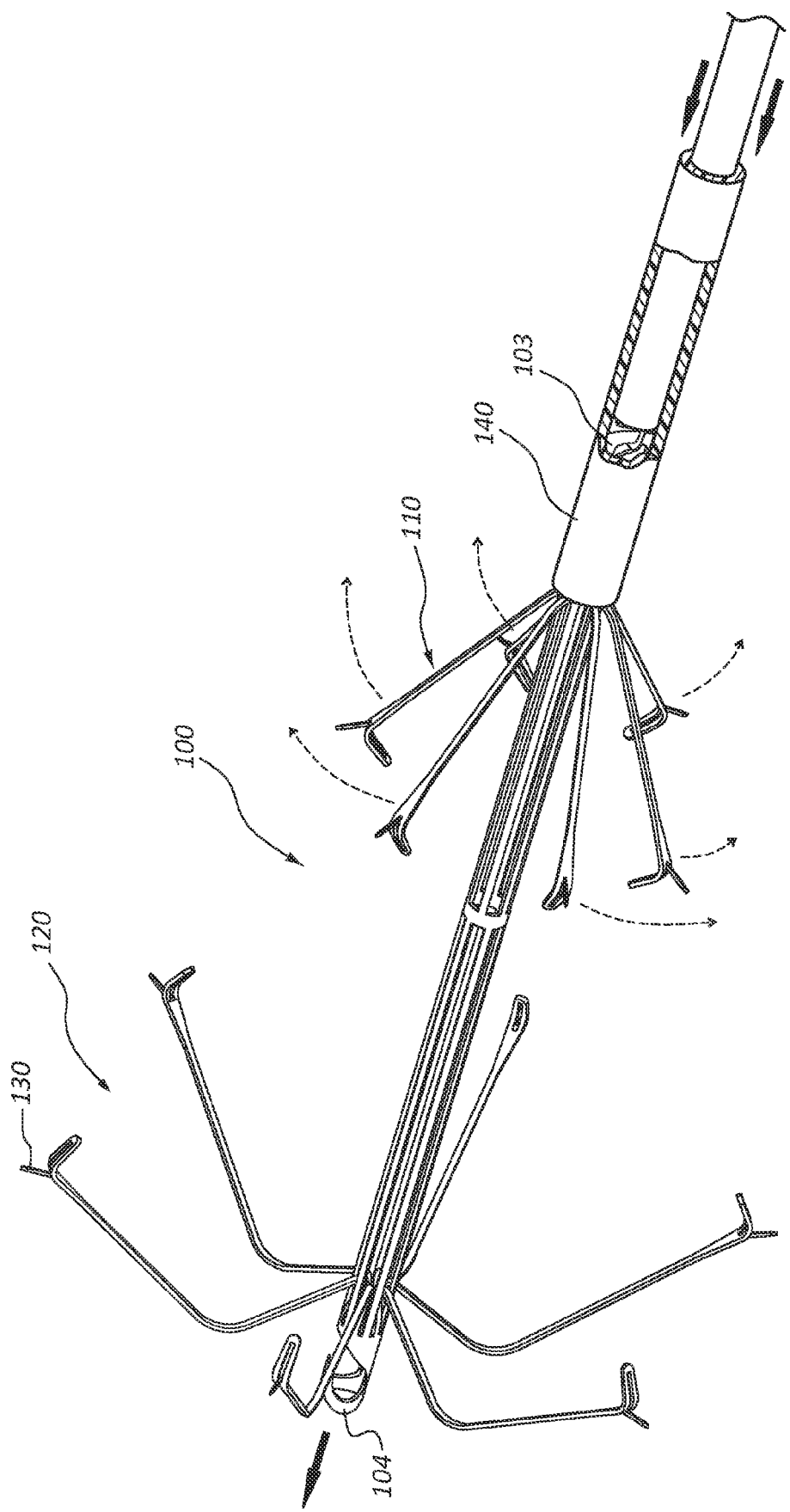
FIG. 5 is a perspective view of the filter 100 of FIG. 1, partially disposed within the catheter 140 of FIG. 4.

FIG. 5 is a perspective view of the filter 100 of FIG. 1, partially disposed within the catheter 140 of FIG. 4. As indicated by the arrows, in FIG. 5, the filter 100 is being deployed from the catheter 140. In some embodiments, the filter 100 may be configured to deploy such that one set of legs 110, 120 expands before the other set of legs 110, 120. For example, in FIG. 5, the second set of legs 120 is fully expanded, while the first set of legs 110 is still partially contained within the catheter 140. Thus, in the illustrated embodiment, the second set of legs 120 (and its associated barbs 130) may contact the wall of a body lumen prior to the first set of legs 110 when the filter 100 is deployed. Analogously, in some instances the filter may be oriented the opposite direction within the catheter 140, with the first set of legs 110 exiting the catheter prior to the second set of legs 120 as the filter 100 is deployed. In such instances, the first set of legs 110 may contact the body lumen before the second set of legs 120.

Filters where one set of legs 110, 120 contact the lumen wall prior to a second set of legs 110, 120 may be configured to stabilize the filter 100 during deployment. For instance, during deployment, interaction of the legs 110, 120 with the catheter 140 may tend introduce a biasing force between the filter 100 and the catheter 140. For example, in the embodiment of FIG. 5, interaction between the first set of legs 110 and the catheter 140 they may exert a biasing force on the catheter 140 as the first set of legs 110 expands out from the catheter 140. This biasing force may make the filter 100 difficult to position during deployment, as the biasing force may cause the filter 100 to "jump" or erratically shift as it is deployed. Thus, in embodiments where one set of legs 110, 120 engage the lumen wall prior to the other set of legs 110, 120, contact between the legs 110, 120 and the lumen wall may stabilize the filter 100 and thus minimize the potential for improper placement of the filter 100 due to movement caused by biasing forces.

Figure 6:
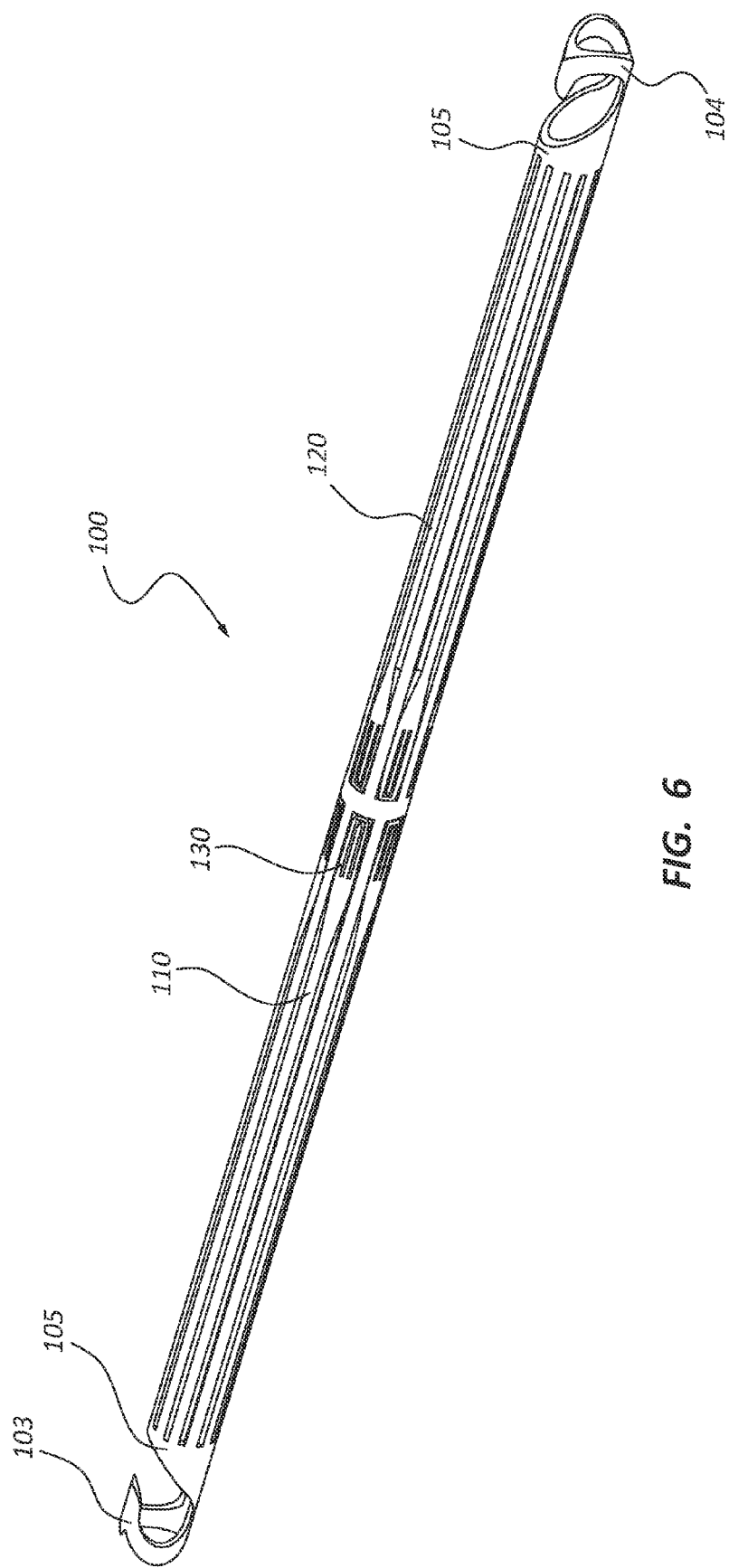
FIG. 6 is a perspective view of filter of FIG. 1 in a pre-expanded state.

FIG. 6 is a perspective view of filter 100 in a pre-expanded state. A filter 100 may be integrally formed from a single tube of material, for example a tube of memory alloy. The shape of each component may first be cut, for example, by laser cutting, and any excess material subsequently removed. The components may then be formed, and set, into the desired shape of the filter 100. FIG. 6 illustrates filter 100, formed from a single tube of material after the tube has been cut and the excess material removed, but before shaping. The tubular portion 105, the first set of legs 110, the second set of legs 120, and the barbs 130 all lie on the same cylinder—the tube from which they were formed—prior to shaping. FIG. 6 also illustrates the proximal 103 and distal 104 hooks of the filter 100.

The examples and embodiments disclosed herein are to be construed as merely illustrative and exemplary, and not a limitation of the scope of the present disclosure in any way. It will be apparent to those having skill in the art with the aid of the present disclosure that changes may be made to the details of the above-described embodiments without departing from the underlying principles of the disclosure herein. It is intended that the scope of the invention be defined by the claims appended hereto and their equivalents.

The invention claimed is:

1. A filter for a body lumen, comprising:
   an axial member having a first end, a second end, and a center axis between the first and second ends,
   a first set of expandable legs, each leg of the first set of legs having an inner end coupled to the axial member and a free outer end configured to be disposed radially outward from the axial member when the first set of legs is expanded, and an outer portion adjacent the outer end, the outer portion forming a curve oriented such that the outer portion curves back toward the axial member when the first set of legs is expanded, a second set of expandable legs, each leg of the second set of legs having an inner end coupled to the axial member and a free outer end configured to be disposed radially outward from the axial member when the second set of legs is expanded, and an outer portion adjacent the outer end, the outer portion forming a curve oriented such that the outer portion curves back toward the axial member when the second set of legs is expanded, wherein each leg comprises, a first substantially straight member coupled to the axial member, and a second substantially straight member coupled to the outer portion and the first substantially straight member, such that, when the legs are expanded, an inner surface of the first substantially straight member and an inner surface of the second substantially straight member define an angle of less than 180 degrees and an outer surface of the axial member and an outer surface of the first substantially straight member define an acute angle; and wherein the first and second sets of legs are circumferentially offset mirror images of each other.

2. The filter of claim 1, wherein the first and second substantially straight members are connected by a curved shoulder.

3. The filter of claim 1, wherein each leg of the first set of expandable legs and the second set of expandable legs further comprise a barb located adjacent to the outer end of the leg, the barb extending radially outward from the longitudinal axis of the axial member.

4. The filter of claim 3, wherein the barbs are formed from center portions of the first and second sets of legs.

5. The filter of claim 3, wherein the barbs associated with the first set of expandable legs are oriented in a different direction than the barbs associated with the second set of expandable legs.

6. The filter of claim 1, wherein the outer portions of the first set of legs are spaced apart from the outer portions of the second set of legs a distance parallel to the longitudinal axis of the axial member, when the first and second sets of legs are expanded.

7. The filter of claim 1, wherein the axial member comprises a tube.

8. The filter of claim 7, wherein the filter is integrally formed from a tube of memory alloy.

9. The filter of claim 1, wherein the inner ends of each leg of the first set of legs and the second set of legs are coupled to a curved intermediate portion, the curved intermediate portion having a first segment which curves inward from the axial member toward the longitudinal axis and a second segment which curves outward toward the radially expanding legs.

10. The filter of claim 1, wherein the first set of legs is configured to engage a body lumen wall before the second set of legs when the filter is deployed.

11. A medical device comprising a filter according to claim 1 disposed within a catheter.

12. A method of filtering clots or other matter in a body lumen, comprising:
obtaining the filter described in claim 1, and disposing the filter within the body lumen of a patient.

13. The method of claim 12, wherein the filter is removably disposed within the body lumen.

14. The method of claim 12, wherein the body lumen is the vasculature.

15. The method of claim 14, wherein the body lumen is the inferior vena cava.

16. A method of deploying a filter, comprising:
inserting a filter into a body lumen, the filter comprising a first set of legs and a second set of legs, wherein the first and second sets of legs are circumferentially offset mirror images of each other;
deploying a first set of legs of the filter, wherein at least two of the legs comprise a first substantially straight member coupled to a second substantially straight member, wherein an inner surface of the first substantially straight member and an inner surface of the second substantially straight member define an angle of less than 180 degrees, and wherein an outer surface of the first substantially straight member and a longitudinal axis of the filter define an acute angle;
contacting the body lumen with the first set of legs;
deploying a second set of legs of the filter, wherein at least two of the legs comprise a first substantially straight member coupled to a second substantially straight member, wherein an inner surface of the first substantially straight member and an inner surface of the second substantially straight member define an angle of less than 180 degrees, and wherein an outer surface of the first substantially straight member and a longitudinal axis of the filter define an acute angle;
stabilizing the filter by contact between the first set of legs and the body lumen while deploying the second set of legs; and
contacting the body lumen with the second set of legs after contacting the body lumen with the first set of legs.

17. The method of claim 16, wherein stabilizing the filter comprises minimizing shift of the filter while the second set of legs deploys.

18. The method of claim 16, wherein contact between the first set of legs and the body lumen partially opposes a biasing force between the second set of legs and a deployment device.

19. An apparatus comprising:
a filter for a body lumen, the filter comprising:
an axial member;
a first set of expandable and compressible legs at a first position along the axial member, the first set of expandable and compressible legs comprising a general umbrella shape with an internal angle of less than 180 degrees; and
a second set of expandable and compressible legs at a second position along the axial member, the second set of expandable and compressible legs comprising a general umbrella shape with an interior angle of less than 180 degrees,
wherein each leg of the first and second sets of expandable and compressible legs comprises a first substantially straight member coupled to the axial member, a second substantially straight member coupled to the first substantially straight member, wherein the axial member and the first substantially straight member of each leg defines an acute exterior angle relative to the general umbrella shape, and wherein the first and second sets of expandable and compressible legs are circumferentially offset mirror images of each other.

20. The apparatus of claim 19, wherein the first and second sets of expandable and compressible legs are configured to be compressible in two directions.

21. The apparatus of claim 20, wherein the first and second sets of expandable and compressible legs are configured to be compressible within a catheter distally and proximally without plastic deformation.

22. The apparatus of claim 19, wherein the axial member and the first and second sets of expandable and compressible legs are integrally formed.

23. The apparatus of claim 19, wherein individual legs of the first and second sets of expandable and compressible legs comprise:
  a first compound curved portion with a first segment which extends toward the center of the axial member and a second segment which extends away from the center of the axial member; and
  a second curved portion at a location radially away from the axial member when the first and second sets of expandable and compressible legs are expanded.

24. The apparatus of claim 23, wherein the first compound curved portion has an inflection point.

25. The apparatus of claim 23, wherein the second segment of the first compound curved portion defines a first radius and the second curved portion defines a second radius, and wherein the first and second radii are different.

26. The apparatus of claim 23, wherein individual legs of the first and second sets of expandable and compressible legs further comprise a third curved portion adjacent free ends thereof.

27. The apparatus of claim 26, wherein the third curved portion comprises a barb.

* * * * *